United States Patent
Lee et al.

(10) Patent No.: US 12,313,538 B2
(45) Date of Patent: May 27, 2025

(54) BIOMOLECULE DETECTION METHOD, COMPUTING DEVICE PERFORMING THE METHOD, AND BIOMOLECULE DETECTION SYSTEM THEREFOR

(71) Applicant: ELECTRONICS AND TELECOMMUNICATIONS RESEARCH INSTITUTE, Daejeon (KR)

(72) Inventors: Won Kyoung Lee, Daejeon (KR); Eon-sang Kim, Daejeon (KR); Sang Rok Moon, Sejong-si (KR); Joon Ki Lee, Sejong-si (KR); Seung-Hyun Cho, Sejong-si (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 236 days.

(21) Appl. No.: 18/307,715

(22) Filed: Apr. 26, 2023

(65) Prior Publication Data
US 2024/0094121 A1     Mar. 21, 2024

(30) Foreign Application Priority Data
Jun. 30, 2022     (KR) .................. 10-2022-0080579

(51) Int. Cl.
  *G01N 21/35*     (2014.01)
  *G01N 21/3577*   (2014.01)
  (Continued)

(52) U.S. Cl.
  CPC ..... *G01N 21/3581* (2013.01); *G01N 21/3577* (2013.01); *A61B 5/0507* (2013.01)

(58) Field of Classification Search
  CPC ............ G01N 21/3581; G01N 21/3577; A61B 5/0507
  See application file for complete search history.

(56) References Cited

U.S. PATENT DOCUMENTS 7,876,423 B1    1/2011    Roth
11,162,900 B2   11/2021   Paulsen et al.
(Continued)

FOREIGN PATENT DOCUMENTS

KR    10-2021-0009134 A    1/2021

OTHER PUBLICATIONS

Christina Chaccour et al., "Seven Defining Features of Terahertz (THz) Wireless Systems: A Fellowship of Communication and Sensing", arXiv:2102.07668v2 [cs.IT], Sep. 25, 2021.
(Continued)

*Primary Examiner* — Hugh Maupin
(74) *Attorney, Agent, or Firm* — Rabin & Berdo, P.C.

(57) ABSTRACT

A method of detecting a biomolecule, a computing device performing the method, and a biomolecule detection system therefor are provided. The method includes receiving a terahertz signal that passed deionized water or reference material, receiving a terahertz signal that passed a target including a predetermined biomolecule, extracting a digital modulation characteristic for the received terahertz signal that passed the deionized water and the received terahertz signal that passed the target, and detecting the predetermined biomolecule included in the target by analyzing the extracted digital modulation characteristic, wherein the received terahertz signal that passed the deionized water and the received terahertz signal that passed the target are generated using a digitally modulated optical signal based on a transmission speed determined based on kinematics of the predetermined biomolecule.

16 Claims, 8 Drawing Sheets

(51) Int. Cl.
*G01N 21/3581* (2014.01)
*A61B 5/0507* (2021.01)

(56) References Cited

U.S. PATENT DOCUMENTS

| | | |
|---|---|---|
| 2014/0198195 A1 | 7/2014 | Jun et al. |
| 2021/0172872 A1 | 6/2021 | Seong et al. |
| 2021/0239611 A1 | 8/2021 | Al-Naib |
| 2023/0107066 A1* | 4/2023 | Ram .................... G01N 33/497 435/4 |

OTHER PUBLICATIONS

Wonkyoung Lee et al., "Noninvasive Glucose Detection Using Digital Modulation Analysis on THz Carriers for Joint Sensing and Communication", Network Research Division, Electronics and Telecommunications Research Institute (ETRI), 2022.

* cited by examiner

Glucode 0mg/dl on schitmer strip

Glucode 200mg/dl on schitmer strip

Glucode 400mg/dl on schitmer strip

BIOMOLECULE DETECTION METHOD, COMPUTING DEVICE PERFORMING THE METHOD, AND BIOMOLECULE DETECTION SYSTEM THEREFOR

CROSS-REFERENCE TO RELATED APPLICATION

This application claims the benefit of Korean Patent Application No. 10-2022-0080579 filed on Jun. 30, 2022, in the Korean Intellectual Property Office, the entire disclosure of which is incorporated herein by reference for all purposes.

BACKGROUND

1. Field of the Invention

The present disclosure relates to a terahertz system integrated with a wireless communication function in a terahertz frequency band and a sensing function.

2. Description of the Related Art

A wireless communication function using a terahertz (THz) frequency band, that is 0.1 THz to 10 THz, may improve transmission speed and transmission capacity of data compared to wireless communication in a conventional millimeter frequency band. In addition, a sensing function using the THz frequency band may enable high-resolution imaging.

More particularly, due to high sensitivity against polar liquid and soft tissue and deionized characteristics of THz radiation, a THz sensing technique may attract attention as an effective alternative technique in the ex vivo as well as in vivo bio-detection and medical diagnosis field.

Particularly, in the sixth generation (6G) wireless network, implementation of a multi-functional wireless system including communication, sensing, positioning, and control techniques may be significantly important to provide an innovative service technique, such as holographic teleportation that is a remote transportation technique based on holograms, an autonomous system, and digital twin.

However, to completely support a service that may be provided by the 6G wireless network, technical limitations, such as free space path loss in the THz frequency band and inefficient power consumption, may need to be overcome. For this, recently, a THz wireless communication technique using a silicon photonic integrated circuit and machine learning-based adaptive beam control has been studied.

In addition, recently, to overcome limitations, such as penetration depth limit and a contrast decrease due to a strong absorption characteristic of a THz signal for water, a medical image technique using a THz penetration enhancer, such as glycerol and gold nanoparticles, has been developed. However, to realize a stably repeatable characteristic of the THz penetration enhancer, there is a disadvantage that an expensive and sophisticated nanoparticle manufacturing process is required.

A conventional system integrating a THz communication function with a sensing function may have a problem that complexity of the system increases due to the use of a dual frequency band since the communication function and sensing function are separated by frequency band.

SUMMARY

Embodiments provide a terahertz system integrating a wireless communication function with a sensing function for detecting a biomolecule included in a target by analyzing a digital modulation characteristic of a terahertz signal used in a communication band in a terahertz frequency band.

According to an aspect, there is provided a method of detecting a biomolecule, the method includes receiving a terahertz signal that passed deionized water or reference material, receiving a terahertz signal that passed a target including a predetermined biomolecule, extracting a digital modulation characteristic for the received terahertz signal that passed the deionized water or reference material and the received terahertz signal that passed the target, and detecting the predetermined biomolecule included in the target by analyzing the extracted digital modulation characteristic, wherein the received terahertz signal that passed the deionized water or reference material and the received terahertz signal that passed the target are generated using a digitally modulated optical signal based on a modulation rate considering dynamics for vibration of the predetermined biomolecules themselves and interaction between the predetermined biomolecule and neighbor molecules.

The extracting includes extracting a digital modulation characteristic corresponding to at least one of an eye diagram, a power spectrum density (PSD), or a constellation diagram for the received terahertz signal that passed the deionized water and the received terahertz signal that passed the target, and the detecting includes determining a concentration of the predetermined biomolecule included in the target by analyzing any combination of the extracted eye diagram, the PSD, and the constellation diagram.

The detecting includes identifying a first eye diagram for the received terahertz signal that passed the deionized water or reference material, identifying a second eye diagram for the received terahertz signal that passed the target, and estimating a concentration of the predetermined biomolecule included in the target by using the cumulative value of the relative intensity difference over time between the identified first eye diagram and the identified second eye diagram.

The detecting includes identifying an intensity difference between an intensity of the received terahertz signal that passed the deionized water and an intensity of the received terahertz signal that passed the target, calculating a PSD by performing frequency conversion on the identified intensity difference, and estimating a concentration of the predetermined biomolecule included in the target by using a PSD value at a peak frequency based on a type of the predetermined biomolecule.

The detecting includes identifying a constellation diagram of the received terahertz signal that passed the target, and estimating a concentration of the predetermined biomolecule included in the target by using a scatter or error vector magnitude of the received terahertz signal that passed the target, wherein the scatter or error vector magnitude is measured by the identified constellation diagram.

According to an aspect, there is provided a computing device includes a processor, a memory configured to load a program executed by the processor, and a storage configured to store the program, wherein the program includes an operation of extracting a digital modulation characteristic for a received terahertz signal that passed deionized water and a received terahertz signal that passed a target including a predetermined biomolecule and detecting the predetermined biomolecule included in the target by analyzing the extracted digital modulation characteristic, wherein the received terahertz signal that passed the deionized water and the received terahertz signal that passed the target are generated using a digitally modulated optical signal based on a modulation rate considering dynamics for vibration of the predetermined biomolecules themselves and interaction between the predetermined biomolecule and neighbor molecules.

The processor is configured to extract a digital modulation characteristic corresponding to at least one of an eye diagram, a PSD, or a constellation diagram for the received terahertz signal that passed the deionized water and the received terahertz signal that passed the target, and estimate a concentration of the predetermined biomolecule included in the target by analyzing any combination of the extracted eye diagram, the PSD, and the constellation diagram.

The processor is configured to identify a first eye diagram for the received terahertz signal that passed the deionized water, identify a second eye diagram for the received terahertz signal that passed the target, and determine a concentration of the predetermined biomolecule included in the target by using the cumulative value of the relative intensity difference over time between the identified first eye diagram and the identified second eye diagram.

The processor is configured to identify an intensity difference between an intensity of the received terahertz signal that passed the deionized water and an intensity of the received terahertz signal that passed the target, calculate a power spectrum density (PSD) by performing frequency conversion on the identified intensity difference, and estimate a concentration of the predetermined biomolecule included in the target by using a PSD value at a peak frequency based on a type of the predetermined biomolecule.

The processor is configured to identify a constellation diagram of the received terahertz signal that passed the target and estimate a concentration of the predetermined biomolecule included in the target by using a scatter of the received terahertz signal that passed the target, wherein the scatter is measured by the identified constellation diagram.

According to an aspect, there is provided a biomolecule detection system includes a transmitter configured to emit, to a target including a predetermined biomolecule, a terahertz signal in a predetermined frequency band generated by using a digitally modulated optical signal, a receiver configured to detect the predetermined biomolecule included in the target by analyzing a digital modulation characteristic for a received terahertz signal that passed the target, wherein the transmitter sends analysis information of the predetermined biomolecule detected by the receiver to an external server using the terahertz signal in the predetermined frequency band.

The terahertz signal in the predetermined frequency band is generated using a digitally modulated optical signal based on a modulation rate considering dynamics for vibration of the predetermined biomolecules themselves and interaction between the predetermined biomolecule and neighbor molecules.

The receiver is configured to determine a concentration of the predetermined biomolecule included in the target by analyzing any combination of the extracted eye diagram, the PSD, and the constellation diagram, which are extracted from the received terahertz signal.

The receiver is configured to determine a concentration of the predetermined biomolecule included in the target by using the cumulative value of the relative intensity difference over time between (i) a first eye diagram for a received terahertz signal that passed deionized water and (ii) a second eye diagram for the received terahertz signal that passed the target.

The receiver is configured to identify an intensity difference between an intensity of the received terahertz signal that passed the deionized water and an intensity of the received terahertz signal that passed the target, calculate a PSD by performing frequency conversion on the identified intensity difference, and determine a concentration of the predetermined biomolecule included in the target by using a PSD value at a peak frequency based on a type of the predetermined biomolecule.

The receiver is configured to determine a concentration of the predetermined biomolecule included in the target by using a scatter of a received terahertz signal that passed the target, wherein the scatter is measured by a constellation diagram of the received terahertz signal that passed the target.

Additional aspects of embodiments will be set forth in part in the description which follows and, in part, will be apparent from the description, or may be learned by practice of the disclosure.

According to embodiments, a biomolecule included in a target may be detected by analyzing a digital modulation characteristic of a terahertz signal used in a communication band in a terahertz frequency band.

Through this, by providing a terahertz system integrating a wireless communication function with a sensing function, the present disclosure may improve sensing sensitivity while decreasing complexity of the system.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1:
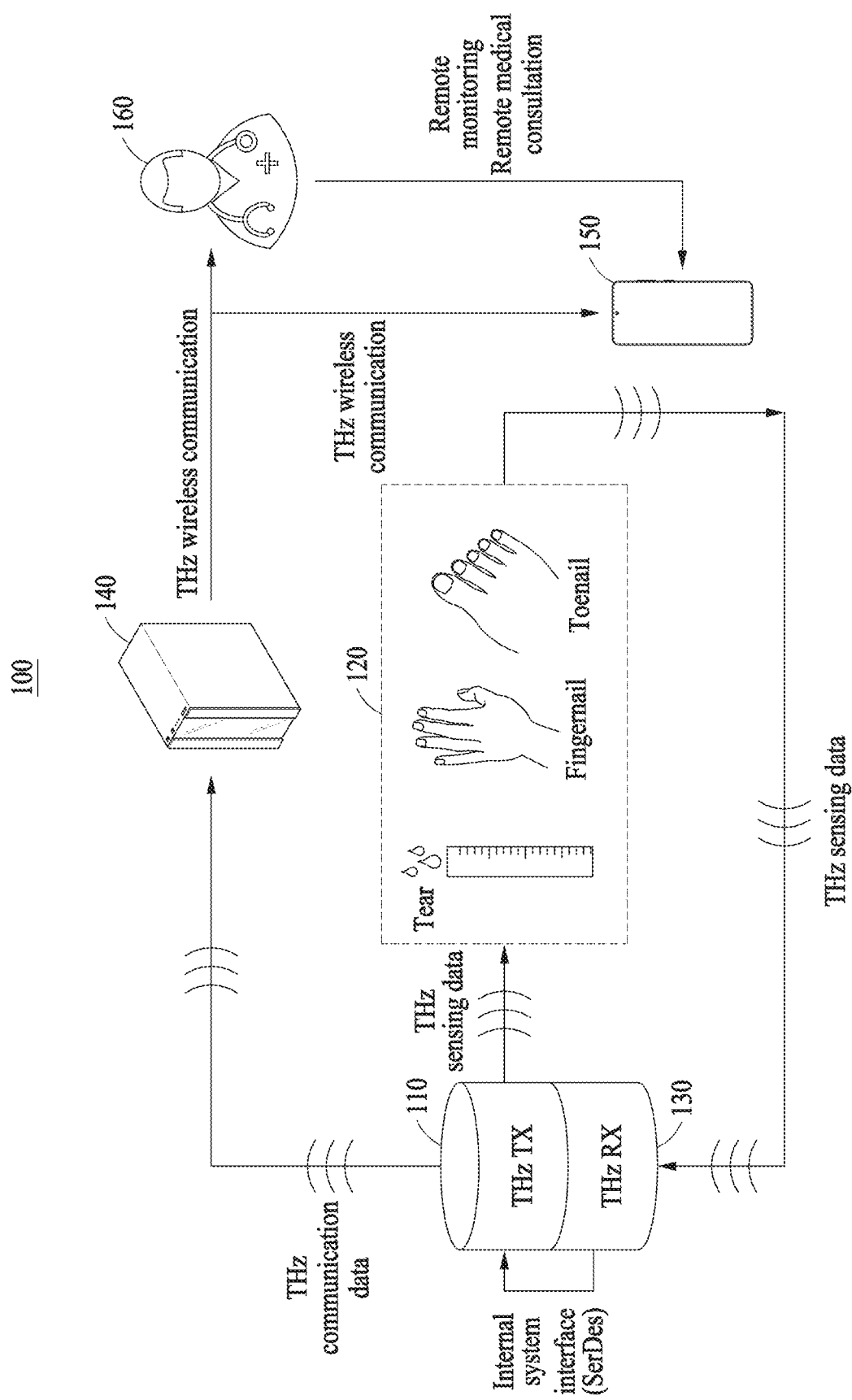
FIG. 1 is a diagram illustrating a terahertz (THz) system according an embodiment.

The following detailed structural or functional description is provided as an example only and various alterations and modifications may be made to the examples. Here, the examples are not construed as limited to the disclosure and should be understood to include all changes, equivalents, and replacements within the idea and the technical scope of the disclosure.

Terms, such as first, second, and the like, may be used herein to describe components. Each of these terminologies is not used to define an essence, order or sequence of a corresponding component but used merely to distinguish the corresponding component from other component(s). For example, a first component may be referred to as a second component, and similarly the second component may also be referred to as the first component.

It should be noted that if one component is described as being "connected", "coupled", or "joined" to another component, a third component may be "connected", "coupled", and "joined" between the first and second components, although the first component may be directly connected, coupled, or joined to the second component.

The singular forms "a," "an," and "the" are intended to include the plural forms as well, unless the context clearly indicates otherwise. As used herein, "A or B", "at least one of A and B", "at least one of A or B", "A, B or C", "at least one of A, B and C", and "at least one of A, B, or C," each of which may include any one of the items listed together in the corresponding one of the phrases, or all possible combinations thereof. It will be further understood that the terms "comprises/including" and/or "includes/including" when used herein, specify the presence of stated features, integers, operations, operations, elements, and/or components, but do not preclude the presence or addition of one or more other features, integers, operations, operations, elements, components and/or groups thereof.

Unless otherwise defined, all terms, including technical and scientific terms, used herein have the same meaning as commonly understood by one of ordinary skill in the art to which this disclosure pertains. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Hereinafter, examples will be described in detail with reference to the accompanying drawings. When describing the examples with reference to the accompanying drawings, like reference numerals refer to like components and a repeated description related thereto will be omitted.

FIG. 1 is a diagram illustrating a terahertz (THz) system according an embodiment.

Diabetes is a chronic hyperglycemic metabolic disorder that causes serious complications such as stroke, high blood pressure, and a coronary artery disease. For early diagnosis and appropriate treatment of diabetes, accurate monitoring of blood glucose may be significantly important. Accordingly, the THz system provided herein may provide a THz sensing technique for non-invasive diabetes measurement that may be integrated with a THz wireless communication technique using a THz frequency band. In this case, blood glucose concentration measurable by the THz system is an example and not limited thereto.

More specifically, referring to FIG. 1, the THz system may be a biomolecule detection system 100 that detects a biomolecule included in a target using a THz signal. A THz transmitter (also referred to as a THz TX) 110 of the biomolecule detection system 100 may generate a THz signal in a predetermined frequency band among THz frequency bands and may emit the THz signal to a target 120 including a predetermined biomolecule. Thereafter, a THz receiver (also referred to as a THz RX) 130 of the biomolecule detection system 100 may non-invasively detect a biomolecule included in the target 120 using the received THz signal in the predetermined frequency band passing through the target 120.

For example, the THz transmitter 110 may generate a THz signal in a frequency band of 0.1 THz to 0.3 THz that is mainly used for communication among the THz frequency band 0.1 THz to 10 THz and may emit the THz signal to the target 120 including a biomolecule, such as tears, a fingernail, and a toenail. Then, the THz receiver 130 may non-invasively detect the biomolecule included in the target 120 by processing and analyzing the received THz signal passing through the target 120.

Thereafter, the THz receiver 130 may generate communication data using analysis information on the detected biomolecule and may transmit the communication data to the THz transmitter 110 through an internal interface (e.g., a Serializer/Deserializer (SerDes)) of the biomolecule detection system 100. The THz transmitter 110 may transmit analysis information on the biomolecule received by the THz receiver 130, that is, the communication data, to an external server 140 using a THz signal in a predetermined frequency band. For example, the external server 140 may be a system providing a personalized health care service using the analysis information on the biomolecule.

In other words, the biomolecule detection system 100 may save costs and easily control and manage the biomolecule detection system 100 through simplification of a system structure by integrating a communication function with a sensing function by setting the same frequency band to a THz signal for detecting a biomolecule included in the target 120 and a THz signal for transmitting analysis information for the detected biomolecule to the external server 140 through the THz receiver 130.

The external server 140 may diagnose a disease of a patient based on analysis information on a biomolecule received by the THz receiver 130 and may enable rapid remote medical consultation of a doctor for a patient by transmitting a diagnosis result to a first user terminal 150 of the patient or a second user terminal 160 of the doctor by using a THz wireless communication technique.

In addition, the THz sensing technique provided herein may provide a method of non-invasively, simply, and accurately detecting a biomolecule included in the target 120 without drawing blood by injecting a THz signal that is modulated in on-off keying (OOK) with a rate of 10 Gbps or more into a biomolecule of the target 120 to be measured and analyzing a digital modulation characteristic of the THz signal that passed the biomolecule. A detailed description of the biomolecule detection method by analyzing a digital modulation characteristic is provided with reference to the drawings.

Figure 2:
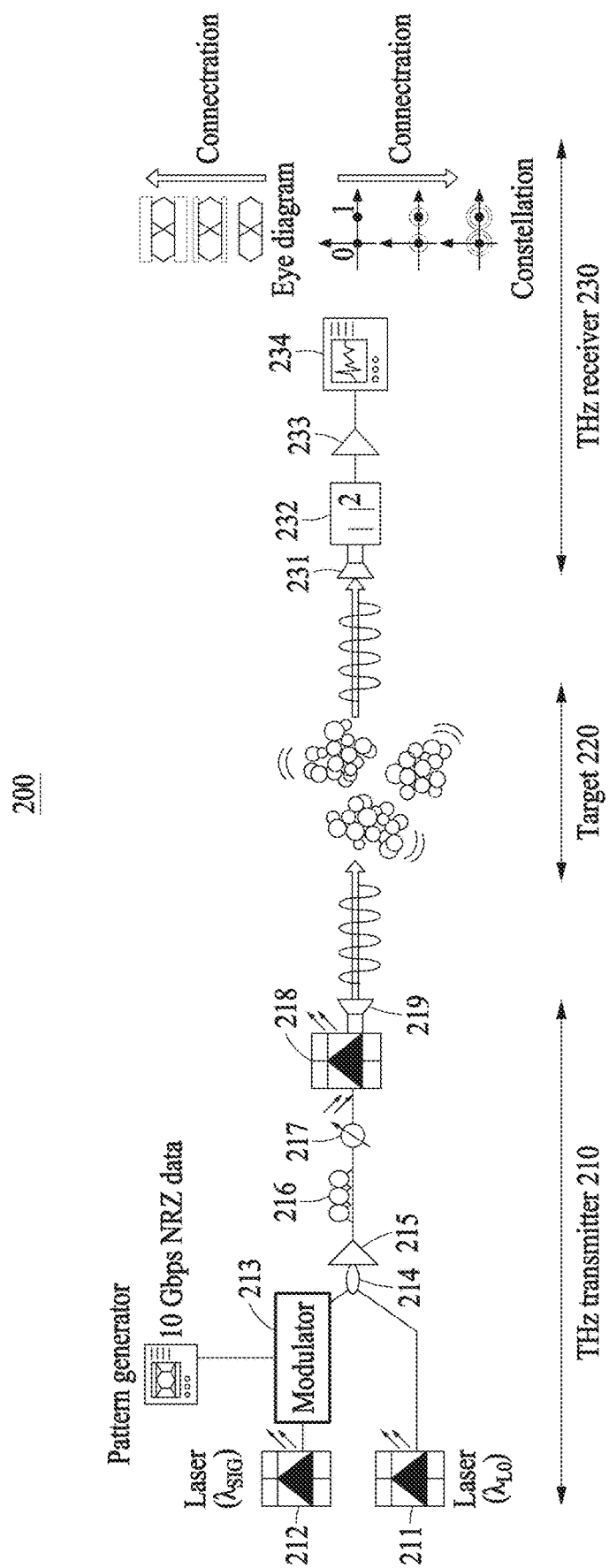
FIG. 2 is a diagram illustrating a biomolecule detection method through a digital modulation characteristic analysis according to an embodiment.

FIG. 2 is a diagram illustrating a biomolecule detection method through a digital modulation characteristic analysis according to an embodiment.

The example of FIG. 2 describes a detection system 200 for non-invasively detecting glucose by analyzing a digital modulation characteristic for a THz signal. The detection system 200 may include a THz transmitter 210 for generating a THz signal based on photonics and modulating a THz signal in various methods, such as OOK or phase shift keying (PSK), a target 220 in which biomolecules to be measured are collected, and a THz receiver 230 for detecting a biomolecule included in the target 220 by analyzing a digital modulation characteristic for a received THz signal that passed through the target 220. In this case, the THz transmitter 210, the target 220, and the THz receiver 230 may respectively correspond to the THz transmitter 110, the target 120, and the THz receiver 130 of FIG. 1.

The THz transmitter 210 may generate a local oscillator (LO) signal that is a continuous wave (CW) optical signal using laser 211 having a peak wavelength $\lambda_{LO}$. The THz transmitter 210 may generate a CW optical signal using laser 212 having a peak wavelength $\lambda_{SIG}$ and may generate an SIG signal by digitally modulating the CW optical signal based on a predetermined transmission speed using a modulator 213. In this case, the modulator 213 may generate the SIG signal using non-return zero (NRZ) data generated by a pattern generator.

For example, the THz transmitter 210 may generate an LO signal using the laser 211 having a peak wavelength of $\lambda_{LO}$. In addition, the THz transmitter 210 may generate a CW optical signal using the laser 212 having a peak wavelength of 1552.4 nm and may generate an SIG signal that is an NRZ optical signal by digitally modulating the CW optical signal using the modulator 213. The SIG signal may be digitally modulated based on a transmission speed considering dynamics for vibration of the predetermined biomolecules themselves and interaction between the predetermined biomolecule and neighbor molecules. For example, to detect a glucose molecule, an SIG signal may be generated by digitally modulating a CW optical signal at a speed of 10 Gbps. However, when a biomolecule to be detected is other than a glucose molecule, the digital modulation speed may vary depending on the biomolecule.

In this case, the THz transmitter 210 may control a wavelength difference between the LO signal and the SIG signal to correspond to a carrier frequency of a THz signal to be generated. In the embodiment, because a wavelength difference of two signals is 2.4 nm, a carrier frequency of a THz signal generated by heterodyne optical beating may correspond to 299.48 GHz.

The THz transmitter 210 may combine the LO signal with the SIG signal using an optical coupler 214 into one signal and may amplify the signal using an optical amplifier (e.g., an erbium-doped fiber amplifier (EDFA)) 215. Polarization of the amplified optical signal may be adjusted by a polarization controller (PC) 216 based on polarization of a uni-traveling-carrier photodiode (UTC-PD) 218 and the intensity of the amplified optical signal may be adjusted by a variable attenuator 217 based on an input condition of the UTC-PD 218.

The UTC-PD 218 included in the THz transmitter 210 may generate a THz signal modulated to 10 Gbps NRZ using heterodyne optical beating of two signals (e.g., the LO signal and the SIG signal) input to the UTC-PD 218 and may emit the generated THz signal modulated to 10 Gbps NRZ to the target 220 using a horn antenna 219.

The THz receiver 230 may receive the THz signal that passed the target 220 using a horn antenna 231. Thereafter, the THz receiver 230 may frequency down-convert the received THz signal into a base band using a Schottky barrier diode (SBD) 232.

The THz receiver 230 may amplify the THz signal that is frequency down-converted into the base band using a radio frequency (RF) amplifier 233 and transmit the THz signal to an oscilloscope 234. The THz receiver 230 may detect, using a separate computing device (not shown), a biomolecule included in the target 220 by analyzing various digital modulation characteristics of a THz signal that is extracted by the oscilloscope 234.

For example, the computing device may determine a biomolecule included in the target 220, that is, concentration of glucose, by analyzing any combination of an eye diagram, a power spectrum density (PSD), and a constellation diagram of the THz signal that is extracted by the oscilloscope 234.

Figure 3A:
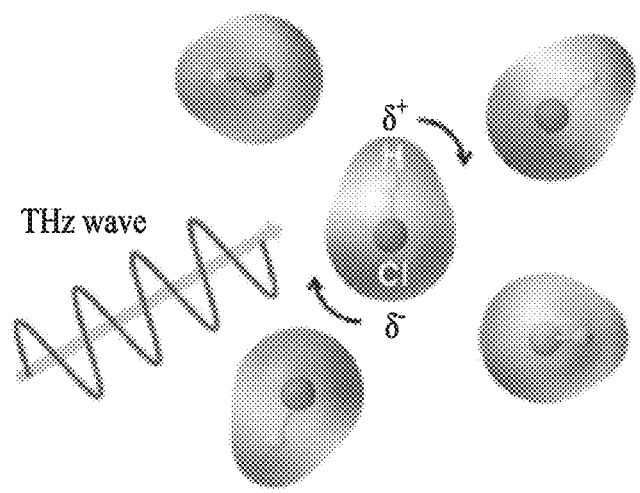
FIGS. 3A and 3B are diagrams illustrating an example of the vibration and interaction between biomolecules excited by a THz signal and an example of resonant frequency movement based on concentration of glucose molecules, according to an embodiment.
Figure 3B:
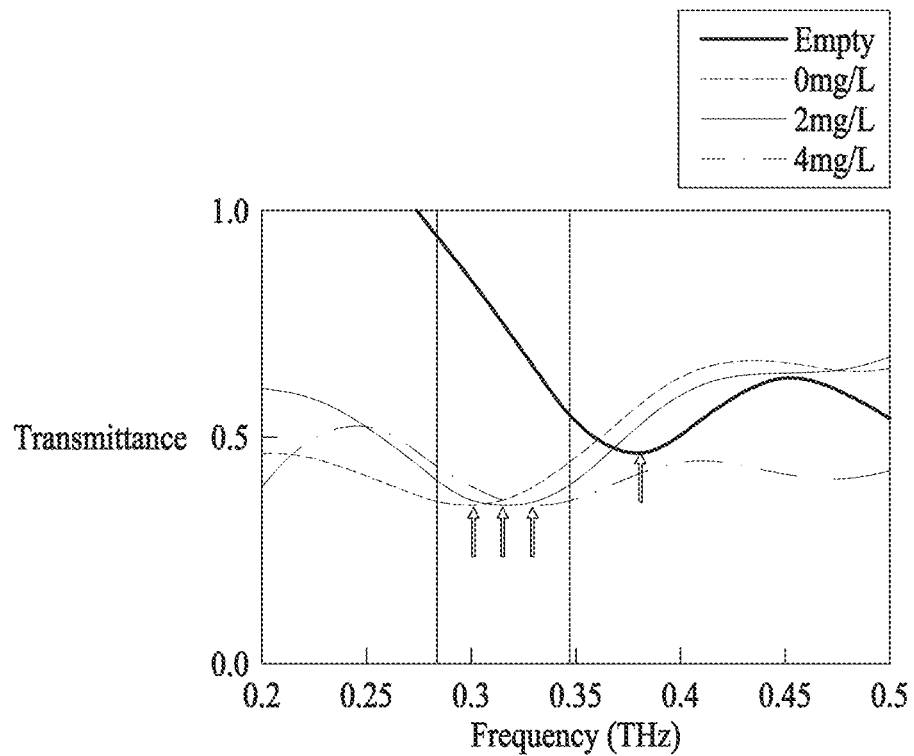

FIGS. 3A and 3B are diagrams illustrating an example of the vibration and interaction between biomolecules excited by a THz signal and an example of resonant frequency movement based on concentration of glucose molecules, according to an embodiment.

Referring to FIG. 3A, an interaction among electronics, spin, and rotational modes of biomolecules, such as glucose, may have a resonant frequency in a THz frequency band and dynamics of the biomolecules may occur in a picosecond (ps) range. Due to this, referring to a transmission spectrum of a THz signal for a glucose solution as shown in FIG. 3B, as the glucose concentration increases, the resonant frequency may shift to a higher frequency.

Accordingly, when energy of a THz signal in a 0.3 THz band is injected into a biomolecule, wherein the THz signal is modulated at the speed of 10 Gbps corresponding to a beat cycle of 100 ps, vibration of biomolecules, more particularly, an interaction in hydrogen bonding may occur and a change in a refractive index may occur thereby. Accordingly, due to this scheme, a radio wave of a THz signal transmitting digital data may be affected and the performance of digital data of a restored THz signal may change.

The detection system 200 herein may detect a biomolecule by analyzing a transmission performance change of digital data wherein the change occurs by injecting a THz signal into a biomolecule. The detection system 200 may accurately detect a subtle change while removing noise through a series of processes of modulating a THz signal in a picosecond time range and restoring digital data from the received THz signal that passed the target 220.

In addition, the detection system 200 may quantitatively analyze concentration of biomolecules included in the target 220 by analyzing a digital modulation characteristic for the digital data of the received THz signal.

Figure 4:
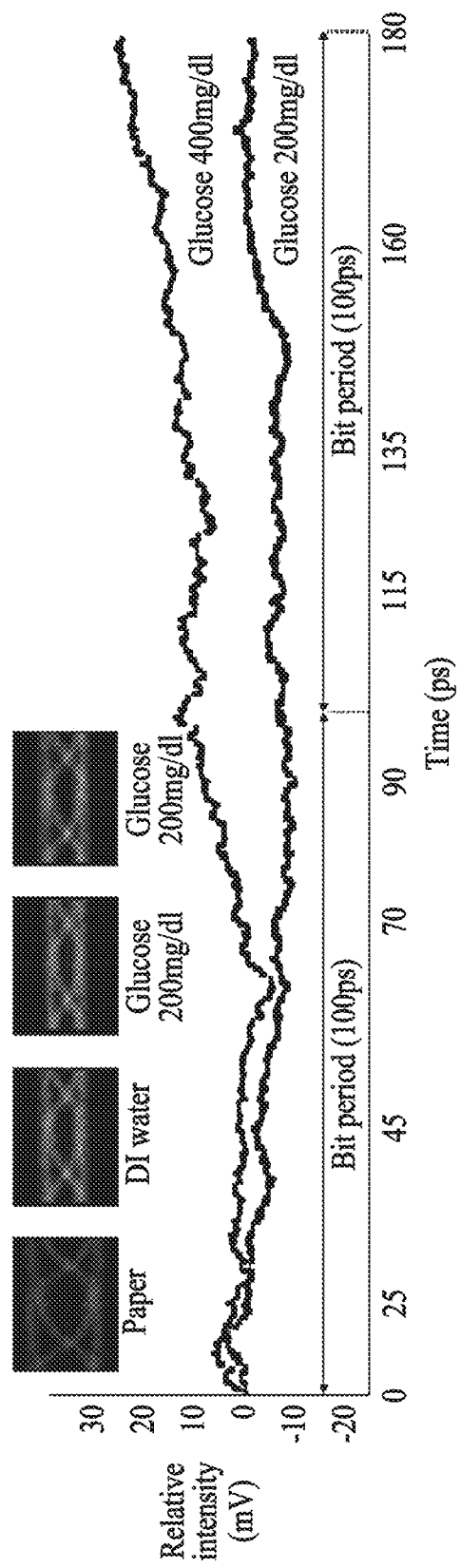
FIGS. 4 and 5 are diagrams illustrating a method of estimating concentration of a biomolecule included in a target by analyzing an eye diagram of a THz signal according to an embodiment.
Figure 5:
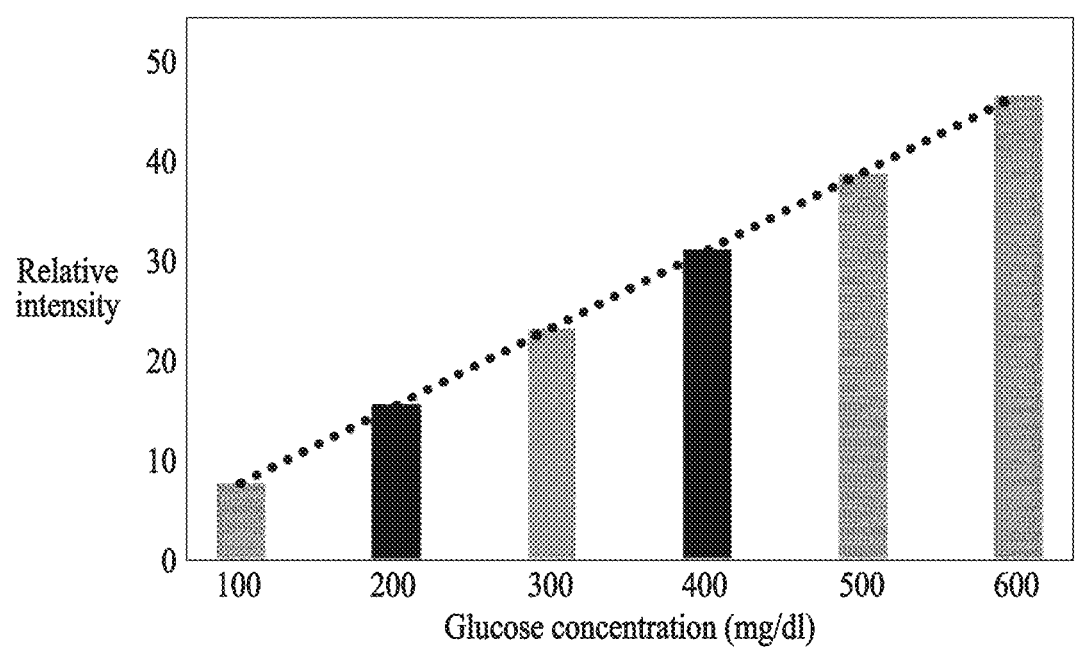

FIGS. 4 and 5 are diagrams illustrating a method of estimating concentration of a biomolecule included in a target by analyzing an eye diagram of a THz signal according to an embodiment.

The detection system 200 may identify a first eye diagram for a received THz signal that passed deionized water and may identify a second eye diagram for a received THz signal that passed a target. In this case, the detection system 200 may determine concentration of biomolecules included in the target by using the cumulative value of the relative intensity difference over time between the identified first eye diagram and the identified second eye diagram.

For example, the detection system 200 may propose a method of detecting glucose by characterizing glucose by concentration by representing an eye diagram as a waterfall chart over time after passing a THz signal modulated to 10 Gbps NRZ through two glucose solution samples having different concentrations.

For this, the detection system 200 may measure eye diagrams for a Schirmer paper strip without a glucose molecule and a sample in which drops of a deionized solution are applied to a Schirmer paper strip. In addition, the detection system 200 may inject glucose molecules into a deionized solution and may apply drops of glucose solutions having two concentrations, 200 mg/dl and 400 mg/dl, to Schirmer paper strips, and may measure eye diagrams thereof.

Referring to the eye diagrams of FIG. 4, there is almost no loss in an eye diagram of a THz signal that passed the Schirmer paper strip without a glucose molecule. On the other hand, referring to eye diagrams of THz signals passing deionized water (e.g., DI water) and glucose solutions (e.g., glucose 200 mg/dl and glucose 400 mg/dl) having different concentrations, eye heights representing an intensity difference between a data level of a symbol "0" and a data level of a symbol "1" significantly decrease compared to an eye height of the THz signal that passed the Schirmer paper strip. This may be a result of absorption of the THz signal by water.

When a glucose molecule is added to deionized water, a change in a refractive index may occur due to the glucose molecule, a resonant frequency of the THz signal may move, and thus, a change in an eye pattern in the eye diagram may occur. To more effectively represent this, FIG. 4 shows a waterfall chart over time representing the cumulative value of the relative intensity difference between a first eye diagram for a received THz signal that passed deionized water and a second eye diagram for a received THz signal that passed a glucose solution. In other words, the waterfall chart may represent a difference between the first eye diagram and the second eye diagram over time.

Referring to FIG. 4, as time elapses, a difference between the eye diagram for the deionized water and the eye diagram for the glucose solution may increase in proportion to concentration. The eye diagram is a tool for indicating how much the THz receiver 230 receives a digitally modulated THz signal that is transmitted by the THz transmitter 210 without distortion. Accordingly, an increase in the difference between eye diagrams as time elapses may represent that due to the glucose solution, a THz signal transmitted by the THz transmitter 210 may be distorted and received by the THz receiver 230. The detection system 200 may determine the glucose concentration by quantifying this phenomenon.

The detection system 200 may quantitatively determine glucose as shown in FIG. 5 by using the cumulative relative intensity difference in a predetermined time slot shown in the waterfall chart of the eye diagram. More particularly, the detection system 200 may organize, in a lookup table in advance, the relative intensity difference in a predetermined time slot by concentration of a biomolecule to be detected. Thereafter, the detection system 200 may quantitatively determine glucose by comparing the lookup table that is organized in advance to the relative intensity difference determined through the eye diagram for the THz signal received in an actual detection step and the eye diagram for deionized water measured in advance. For example, FIG. 5 illustrates an example of determining glucose using the cumulative relative intensity difference after two beat cycles (e.g., 200 ps).

Figure 6:
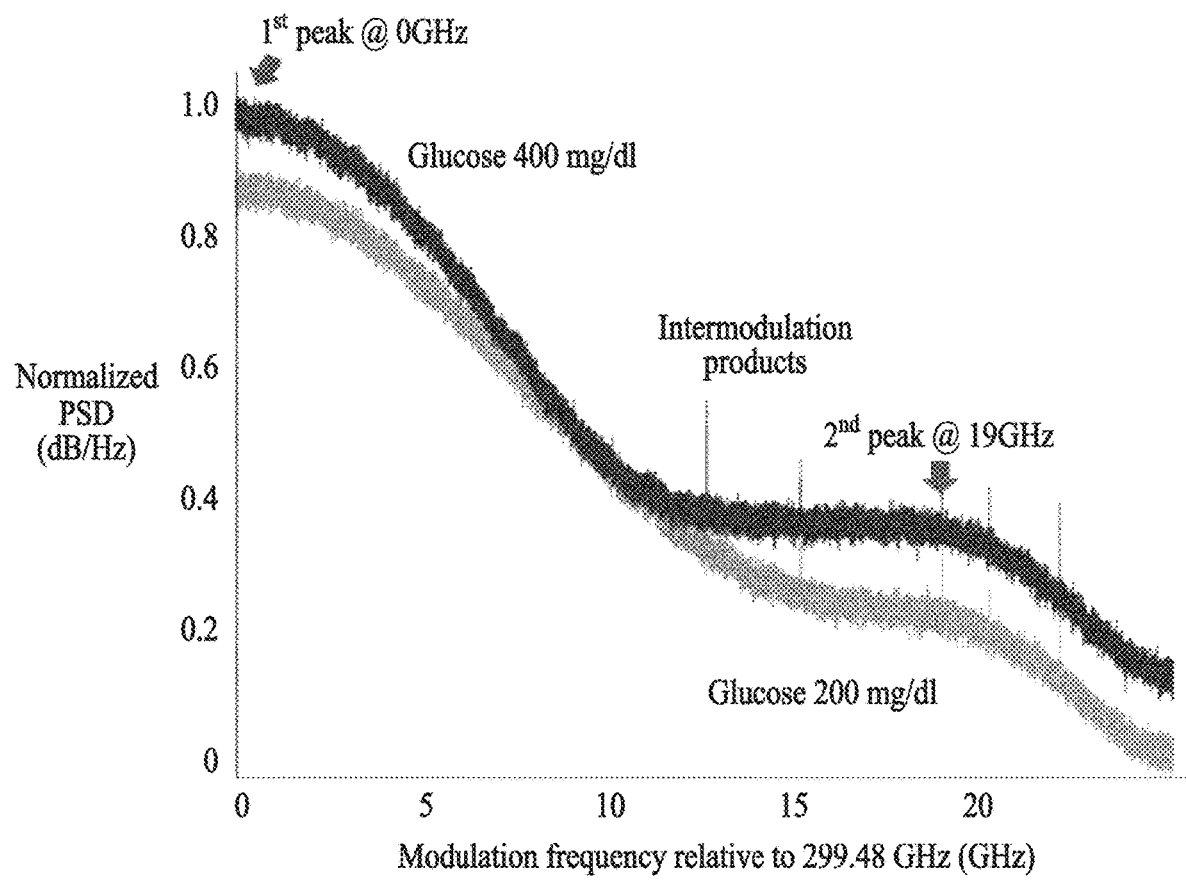
FIGS. 6 and 7 are diagrams illustrating a method of estimating concentration of a biomolecule included in a target by analyzing a power spectrum density (PSD) of a THz signal according to an embodiment.
Figure 7:
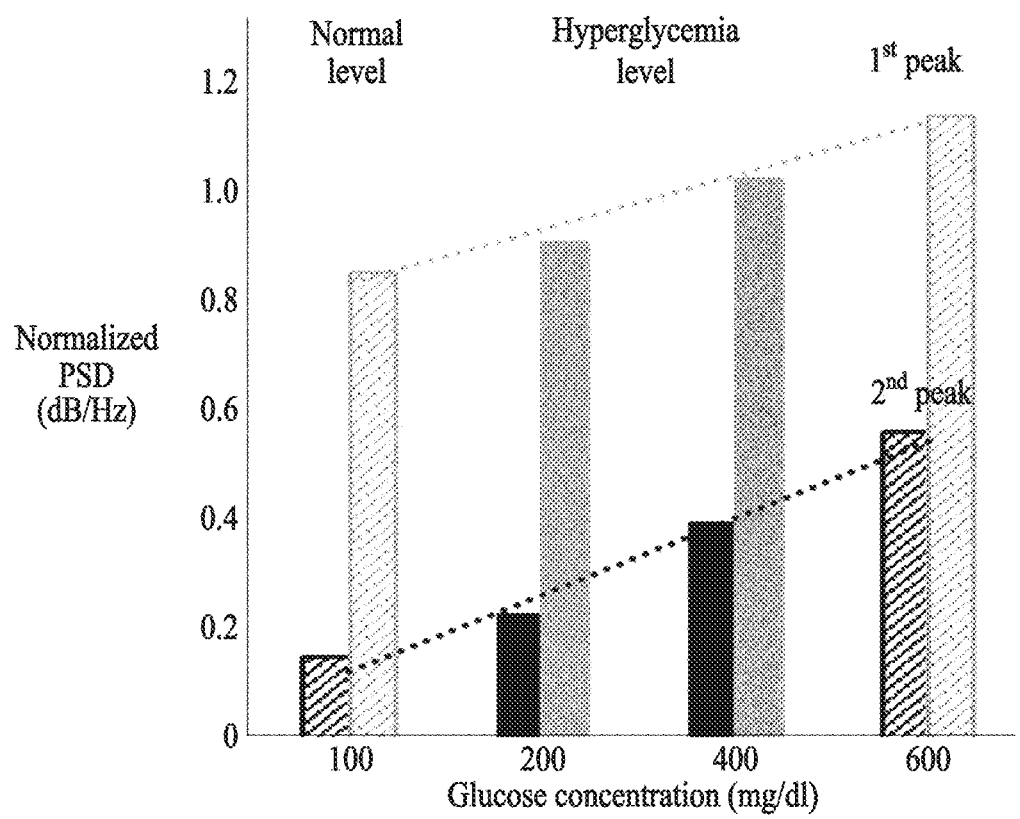

FIGS. 6 and 7 are diagrams illustrating a method of estimating concentration of a biomolecule included in a target by analyzing a power spectrum density (PSD) of a THz signal according to an embodiment.

The detection system 200 may identify an intensity difference between an intensity of a received THz signal that passed deionized water and an intensity of a received THz signal that passed a glucose solution and may calculate a PSD by performing conversion on the identified intensity difference from a time function to a frequency function. Thereafter, the detection system 200 may determine concentration of biomolecules included in a target using a PSD value at a peak frequency based on a predetermined biomolecule type.

For example, the detection system 200 may propose a method of quantitatively detecting glucose by measuring a PSD based on a relative modulation frequency for a carrier frequency of a THz signal. FIG. 6 is a graph representing, as a PSD, an intensity (voltage) difference between a THz signal that passed two glucose solutions, of which concentrations are 200 mg/dl and 400 mg/dl, and a THz signal that passed deionized water.

In this case, as shown in FIG. 7, based on a PSD at a predetermined peak frequency for glucose, that is, at 0 GHz and 19 GHz, the PSD may increase in proportion to concentrations at the two predetermined peak frequencies. Accordingly, the detection system 200 may determine concentration of a biomolecule through the PSD at a predetermined peak frequency for each biomolecule type.

For this, the detection system 200 may organize, in a lookup table in advance, a PSD value at a peak frequency based on the predetermined biomolecule type. Thereafter, the detection system 200 may quantitatively determine glucose by comparing the pre-organized lookup table to a PSD value determined through an intensity of a THz signal received in an actual detection step and a pre-measured intensity of deionized water.

However, because PSD values corresponding to all concentrations may not be measured and stored in the lookup table, the detection system 200 may determine a range of PSD values by a predetermined unit and when a PSD value measured in an actual detection step falls inside a PSD value range of predetermined concentration, the detection system 200 may determine that the measured PSD value is the predetermined unit.

Figure 8:
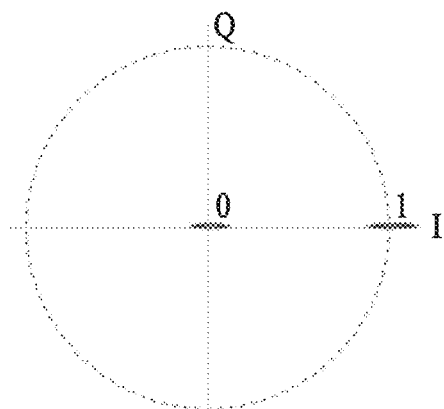
FIG. 8 is a diagram illustrating a method of estimating concentration of a biomolecule included in a target by analyzing a constellation diagram of a THz signal, according to an embodiment.
Figure 8:
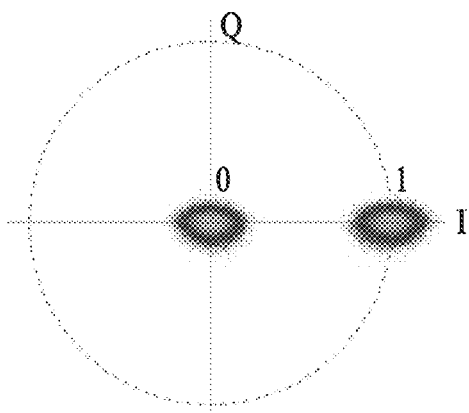
Figure 8:
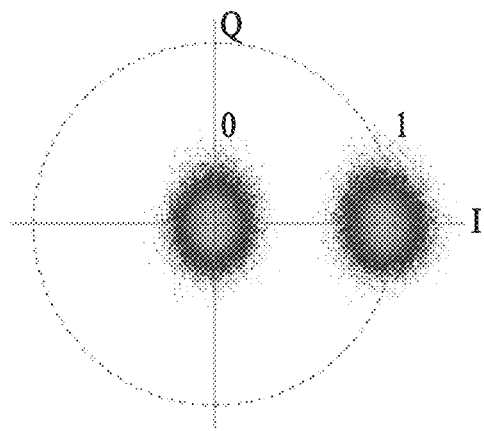

FIG. 8 is a diagram illustrating a method of estimating concentration of a biomolecule included in a target by analyzing a constellation diagram of a THz signal, according to an embodiment.

The detection system 200 may identify a constellation diagram of a received THz signal that passed a target including a biomolecule and may determine concentration of the biomolecule included in the target by using dispersion of a THz signal measured in the identified constellation diagram.

For example, FIG. 8 illustrates constellation diagrams of a 10 Gbps modulated signal for glucose solutions having different concentrations. The constellation diagram is a graph representing dispersion of a THz signal on an IQ plane that is a complex plane for an NRZ signal that is modulated by OOK.

As shown in a top diagram of FIG. 8, based on a constellation diagram of a THz signal that passed a Schirmer paper strip without a glucose molecule, it may be identified that scatter is not large. On the other hand, it may be identified that as glucose concentration increases, scatter of a THz signal passing through a Schirmer paper strip increases.

This is because, as the glucose concentration increases, a change in refractive index of the THz signal may increase, and thus, a change in the size and phase of the transmitted THz signal may increase and distortion of restored digital data may increase.

Accordingly, the detection system 200 may quantitatively detect glucose by calculating distortion of digital data using a constellation diagram for a received THz signal. More particularly, the detection system 200 may organize, in a lookup table in advance, the size and shape of constellation by calculating the constellation through an error vector magnitude (EVM) for each predetermined biomolecule. Thereafter, the detection system 200 may calculate EVM for a THz signal received in an actual detection step and may quantitatively determine glucose by comparing the pre-organized lookup table to the calculated EVM.

The components described in the example embodiments may be implemented by hardware components including, for example, at least one digital signal processor (DSP), a processor, a controller, an application-specific integrated circuit (ASIC), a programmable logic element, such as a field programmable gate array (FPGA), other electronic devices, or combinations thereof. At least some of the functions or the processes described in the example embodiments may be implemented by software, and the software may be recorded on a recording medium. The components, the functions, and the processes described in the example embodiments may be implemented by a combination of hardware and software.

The units described herein may be implemented using a hardware component, a software component and/or a combination thereof. A processing device may be implemented using one or more general-purpose or special-purpose computers, such as, for example, a processor, a controller and an arithmetic logic unit (ALU), a DSP, a microcomputer, an FPGA, a programmable logic unit (PLU), a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and multiple types of processing elements. For example, the processing device may include a plurality of processors, or a single processor and a single controller. In addition, different processing configurations are possible, such as parallel processors.

The software may include a computer program, a piece of code, an instruction, or some combination thereof, to independently or uniformly instruct or configure the processing device to operate as desired. Software and data may be embodied permanently or temporarily in any type of machine, component, physical or pseudo equipment, computer storage medium or device, or in a propagated signal wave capable of providing instructions or data to or being interpreted by the processing device. The software also may be distributed over network-coupled computer systems so that the software is stored and executed in a distributed fashion. The software and data may be stored by one or more non-transitory computer-readable recording mediums.

The methods according to the above-described examples may be recorded in non-transitory computer-readable media including program instructions to implement various operations of the above-described examples. The media may also include, alone or in combination with the program instructions, data files, data structures, and the like. The program instructions recorded on the media may be those specially designed and constructed for the purposes of examples, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher-level code that may be executed by the computer using an interpreter.

The above-described devices may be configured to act as one or more software modules in order to perform the operations of the above-described examples, or vice versa.

As described above, although the examples have been described with reference to the limited drawings, a person skilled in the art may apply various technical modifications and variations based thereon. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

What is claimed is:

1. A method of detecting a biomolecule, the method comprising:
   receiving a terahertz signal that passed deionized water or reference material;
   receiving a terahertz signal that passed a target comprising a predetermined biomolecule;
   extracting a digital modulation characteristic for the received terahertz signal that passed the deionized water or reference material and the received terahertz signal that passed the target; and
   detecting the predetermined biomolecule comprised in the target by analyzing the extracted digital modulation characteristic,
   wherein the received terahertz signal that passed the deionized water or reference material and the received terahertz signal that passed the target are generated using a digitally modulated optical signal based on a transmission speed determined based on dynamics for vibration of the predetermined biomolecules themselves and interaction between the predetermined biomolecule and neighbor molecules.

2. The method of claim 1, wherein the extracting comprises extracting a digital modulation characteristic corresponding to at least one of an eye diagram, a power spectrum density (PSD), or a constellation diagram for the received terahertz signal that passed the deionized water and the received terahertz signal that passed the target, and
   the detecting comprises determining a concentration of the predetermined biomolecule comprised in the target by analyzing any combination of the extracted eye diagram, the PSD, and the constellation diagram.

3. The method of claim 1, wherein the detecting comprises:
   identifying a first eye diagram for the received terahertz signal that passed the deionized water or reference material;
   identifying a second eye diagram for the received terahertz signal that passed the target; and
   estimating a concentration of the predetermined biomolecule comprised in the target by using the cumulative value of the relative intensity difference over time between the identified first eye diagram and the identified second eye diagram.

4. The method of claim 1, wherein the detecting comprises:
   identifying an intensity difference between an intensity of the received terahertz signal that passed the deionized water or reference material and an intensity of the received terahertz signal that passed the target;

calculating a power spectrum density (PSD) by performing frequency conversion on the identified intensity difference; and estimating a concentration of the predetermined biomolecule comprised in the target by using a PSD value at a peak frequency based on a type of the predetermined biomolecule.

5. The method of claim 1, wherein the detecting comprises:

identifying a constellation diagram of the received terahertz signal that passed the target; and estimating a concentration of the predetermined biomolecule comprised in the target by using a scatter or error vector magnitude of the received terahertz signal that passed the target, wherein the scatter or error vector magnitude is measured by the identified constellation diagram.

6. A computing device comprising:

a processor;

a memory configured to load a program executed by the processor; and a storage configured to store the program, wherein the program comprises an operation of extracting a digital modulation characteristic for a received terahertz signal that passed deionized water and a received terahertz signal that passed a target comprising a predetermined biomolecule and detecting the predetermined biomolecule comprised in the target by analyzing the extracted digital modulation characteristic, wherein the received terahertz signal that passed the deionized water and the received terahertz signal that passed the target are generated using a digitally modulated optical signal based on a transmission speed determined based on dynamics for vibration of the predetermined biomolecules themselves and interaction between the predetermined biomolecule and neighbor molecules.

7. The computing device of claim 6, wherein the processor is configured to:

extract a digital modulation characteristic corresponding to at least one of an eye diagram, a power spectrum density (PSD), or a constellation diagram for the received terahertz signal that passed the deionized water and the received terahertz signal that passed the target, and estimate a concentration of the predetermined biomolecule comprised in the target by analyzing any combination of the extracted eye diagram, the PSD, and the constellation diagram.

8. The computing device of claim 6, wherein the processor is configured to:

identify a first eye diagram for the received terahertz signal that passed the deionized water, identify a second eye diagram for the received terahertz signal that passed the target, and determine a concentration of the predetermined biomolecule comprised in the target by using the cumulative value of the relative intensity difference over time between the identified first eye diagram and the identified second eye diagram.

9. The computing device of claim 6, wherein the processor is configured to:

identify an intensity difference between an intensity of the received terahertz signal that passed the deionized water and an intensity of the received terahertz signal that passed the target, calculate a power spectrum density (PSD) by performing frequency conversion on the identified intensity difference, and estimate a concentration of the predetermined biomolecule comprised in the target by using a PSD value at a peak frequency based on a type of the predetermined biomolecule.

10. The computing device of claim 6, wherein the processor is configured to:

identify a constellation diagram of the received terahertz signal that passed the target and estimate a concentration of the predetermined biomolecule comprised in the target by using a scatter of the received terahertz signal that passed the target, wherein the scatter is measured by the identified constellation diagram.

11. A biomolecule detection system comprising:

a transmitter configured to emit, to a target comprising a predetermined biomolecule, a terahertz signal in a predetermined frequency band generated by using a digitally modulated optical signal;

a receiver configured to detect the predetermined biomolecule comprised in the target by analyzing a digital modulation characteristic for a received terahertz signal that passed the target, wherein the transmitter sends analysis information of the predetermined biomolecule detected by the receiver to an external server using the terahertz signal in the predetermined frequency band.

12. The biomolecule detection system of claim 11, wherein the terahertz signal in the predetermined frequency band is generated using a digitally modulated optical signal based on a modulation rate considering dynamics for vibration of the predetermined biomolecules themselves and interaction between the predetermined biomolecule and neighbor molecules.

13. The biomolecule detection system of claim 11, wherein the receiver is configured to determine a concentration of the predetermined biomolecule comprised in the target by analyzing any combination of an eye diagram, a power spectrum density (PSD), and a constellation diagram, which are extracted from the received terahertz signal.

14. The biomolecule detection system of claim 11, wherein the receiver is configured to determine a concentration of the predetermined biomolecule comprised in the target by using the cumulative value of the relative intensity difference over time between (i) a first eye diagram over time for a received terahertz signal that passed deionized water and (ii) a second eye diagram over time for the received terahertz signal that passed the target.

15. The biomolecule detection system of claim 11, wherein the receiver is configured to identify an intensity difference between an intensity of the received terahertz signal that passed the deionized water and an intensity of the received terahertz signal that passed the target, calculate a power spectrum density (PSD) by performing frequency conversion on the identified intensity difference, and determine a concentration of the predetermined biomolecule comprised in the target by using a PSD value at a peak frequency based on a type of the predetermined biomolecule.

16. The biomolecule detection system of claim 11, wherein the receiver is configured to determine a concentration of the predetermined biomolecule comprised in the target by using a scatter of a received terahertz signal that passed the target, wherein the scatter is measured by a constellation diagram of the received terahertz signal that passed the target.

* * * * *